United States Patent [19]

Oi et al.

[11] Patent Number: 5,705,101
[45] Date of Patent: Jan. 6, 1998

[54] NEAR INFRARED ABSORBER, PREPARATION PROCESS THEREFOR AND USE THEREOF

[75] Inventors: Ryu Oi; Kazuhiro Seino; Keisuke Takuma, all of Kanagawa-ken, Japan

[73] Assignees: Mitsui Toatsu Chemicals, Inc., Tokyo; Yamamoto Chemicals Inc., Yao, both of Japan

[21] Appl. No.: 572,893

[22] Filed: Dec. 18, 1995

[30] Foreign Application Priority Data

Dec. 21, 1994 [JP] Japan ................................. 6-318191

[51] Int. Cl.$^6$ ..................... F21V 9/04; C09B 47/04
[52] U.S. Cl. .................. 252/587; 540/125; 540/139; 540/140
[58] Field of Search ..................... 252/587; 540/125, 540/139, 140

[56] References Cited

U.S. PATENT DOCUMENTS

| | | |
|---|---|---|
| 4,606,859 | 8/1986 | Duggan et al. . |
| 4,755,012 | 7/1988 | Kojima . |
| 4,778,128 | 10/1988 | Barlow .................. 540/139 |
| 5,124,067 | 6/1992 | Itoh et al. . |
| 5,296,162 | 3/1994 | Itoh et al. . |
| 5,409,634 | 4/1995 | Itoh et al. . |
| 5,516,899 | 5/1996 | Campbell et al. ............ 540/139 |
| 5,582,774 | 12/1996 | Itoh et al. ................. 252/587 |

FOREIGN PATENT DOCUMENTS

| | | |
|---|---|---|
| 0282181 | 9/1988 | European Pat. Off. . |
| 0408191 | 1/1991 | European Pat. Off. . |
| 0519423 | 12/1992 | European Pat. Off. . |
| 51549 | 5/1975 | Japan . |
| 25060 | 8/1979 | Japan . |
| 1311 | 1/1984 | Japan . |
| 152685 | 7/1986 | Japan . |
| 223056 | 10/1986 | Japan . |
| 270765 | 11/1988 | Japan . |
| 308073 | 12/1988 | Japan . |
| 5155 | 1/1990 | Japan . |
| 311447 | 12/1990 | Japan . |
| 75916 | 12/1992 | Japan . |
| 805562 | 12/1958 | United Kingdom . |

OTHER PUBLICATIONS

Patent Abstracts Of Japan, vol. 013, No. 084, (C-572), Feb. 27, 1989 & JP-63-270765 A (Mitsui Toatsu Chemicals, Inc.), Nov. 1988 *abstract*.

*Primary Examiner*—Philip Tucker
*Attorney, Agent, or Firm*—Burns, Doane, Swecker & Mathis

[57] ABSTRACT

A phthalocyanine near infrared absorber having a broad absorption range in the near infrared region and represented by the following formula (1):

$$\left( Y_m \underset{\substack{| \\ Z-CH-CH-N \\ | \ | \ | \\ R^1 \ R^2 \ H}}{\overset{}{\diagup\!\!\!\diagdown}} S \right)_p \underset{M}{\overset{X_r}{-Pc-}} \left( \underset{\substack{| \\ CH-CH-Z \\ | \ | \\ R^1 \ R^2}}{\overset{S}{\diagup\!\!\!\diagdown}} Y_m \right)_q \quad (1)$$

wherein each of the groups is defined.

9 Claims, 5 Drawing Sheets

NEAR INFRARED ABSORBER, PREPARATION PROCESS THEREFOR AND USE THEREOF

BACKGROUND OF THE INVENTION

1. Field of the Invention

This invention relates to phthalocyanine near infrared absorbers having a broad absorption range in the near infrared region, a preparation process therefor, and also near infrared absorbing compositions and heat-ray absorbing filters comprising these absorbers.

A near infrared absorbing compound can be used in a recording layer of an optical recording medium such as an optical disc or the like or, after formulation into an ink, can be employed as a near infrared absorbing ink readable by a near infrared detector. It can also be applied to plastics or glasses after being combined with a binder resin and then formed into a resin composition (coating formulation) or can be kneaded with a resin and formed into a heat-ray absorbing filter adopted to absorb near infrared rays.

The near infrared absorbing filter can shut out heat rays from the outside as a window material for, e.g., buildings, automobiles, trains, ships and airplanes, thereby suppressing a temperature increase inside of a room or vehicle. It can cut off rays in a particular wavelength range so that it can be used for controlling plant growth as an agricultural film making use of its optical selectivity, for intercepting infrared rays to a semiconductor photodetector, and for protecting our eyes from harmful rays including infrared rays as eye glasses or the like.

Among these applications, heat-ray absorbing filters for the interception of heat rays have drawn a particular attention because they contribute to energy saving.

2. Description of the Related Art

Heat reflecting filters in which a metal oxide such as indium oxide or tin oxide and a metal such as gold or silver are alternately laminated on a PET film or glass are known as window materials for the interception of heat rays. However, such heat reflecting filters are accompanied with the drawback that the cost for producing them is high due to their complex production steps, and also become a cause for radio interference. A heat-ray absorbing glass having metal ions dispersed therein also involves a significant problem in cost or the like. Compared with such inorganic heat reflecting filters and heat-ray absorbing glass, heat absorbing filters making use of a near infrared absorbing pigment can be produced easily and are free of radio interference problems, so that they are useful for a wide variety of application fields and are much in demand on the market. It is however the present situation that these filters have not yet found widespread commercial utility because of problems in the cost and durability, particularly, light fastness of the pigment.

Cyanine pigments have heretofore been known well as organic pigments capable of absorbing near infrared rays. These cyanine pigments, however, have extremely low light fastness so that many limitations are unavoidably imposed on their use. The aminium-salt-type compounds disclosed in Japanese Patent Laid-Open No. 311447/1990 or the metal complex compounds disclosed in Japanese Patent Publication No. 25060/1979 and Japanese Patent Laid-Open No. 51549/1975 are insufficient in both heat resistance and light fastness. The anthraquinone compounds disclosed in Japanese Patent Laid-Open Nos. 115362/1991 or 903/1987 (U.S. Pat. No. 4,755,012) are insufficient in light fastness although they have sufficient heat resistance.

Phthalocyanines are disclosed as near infrared absorbing pigments or dyes having high durability, in Japanese Patent Publication Nos. 1311/1984 and 5155/1990 and Japanese Patent Laid-Open Nos. 209583/1985. (U.S. Pat. No. 4,606, 859), 152685/1986, 223056/1986 and 62878/1991 (U.S. Pat. Nos. 5,124,067, 5,296,162, 5,409,634) and the like. They however require complex preparation steps and moreover, are insufficient for absorption of heat rays because of $\lambda_{max}$ of as short as at most 800 nm and an absorption only in a narrow wavelength range.

In Japanese Patent Publication No. 75916/1992, a pigment having $\lambda_{max}$ of 909 nm was obtained in one of the Examples by reacting a chlorinated copper phthalocyanine and 2-aminothiophenol. The above maximum absorption was however measured in pyridine, and there is no disclosure about data on the maximum absorption of the pigment as measured after being coated on a glass plate, the extinction coefficient and the like. Due to the low solubility in an organic solvent or a resin, the above compound develops a hazing phenomenon when dissolved in the resin so that it is impossible to obtain a transparent resin composition or heat-ray absorbing filter from the compound. In the claims of the above publication, a compound having a $C_{1-4}$ substituent is disclosed. However, one to four carbon atoms are so few that the hazing phenomenon cannot be prevented. Moreover, the publication does not contain any disclosure about the preparation process of the compound.

Japanese Patent Laid-Open No. 308073/1988 discloses a process in which a phthalocyanine is reacted in the presence of 2-aminothiophenol and 4-methylphenylthiol to increase its solubility, but the pigment so obtained has $\lambda_{max}$ as short as 890 nm.

On the other hand, Japanese Patent Laid-Open No. 270765/1988 discloses a process for improving both the solubility and absorbable wavelength range of a perchlorocopper phthalocyanine ("Phthalocyanine Green", trade name) by reacting it with 2-aminothiophenol and then alkylating its nitrogen atoms with an alkyl bromide. The pigment so obtained has a maximum absorption wavelength at near 900 nm and has a relatively broad absorption peak, so that it shows a comparatively broad absorption in the near infrared region of 700 to 1,800 nm. It is however still insufficient compared with inorganic near infrared absorbing materials. Moreover, this post-alkylation process cannot perform efficient alkylation so that the resulting pigment may not have sufficiently high solubility in some instances.

SUMMARY OF THE INVENTION

An object of the present invention is to easily provide at a low cost a phthalocyanine near infrared absorbing compound having high light fastness, high solubility and a wide absorption range in the near infrared region (700 to 1,800 nm). Another object of the present invention is to provide a near infrared absorbing compound which is useful as a near infrared absorbing resin composition or a heat-ray absorbing filter.

The present inventors have conducted extensive research with a view toward attaining the above objects. As a result, it has been found that certain types of phthalocyanine near infrared absorbers have excellent performances, leading to the completion of the invention.

In a first aspect of this invention, there is thus provided a phthalocyanine near infrared absorber having a broad absorption range in the near infrared region and represented by the following formula (1):

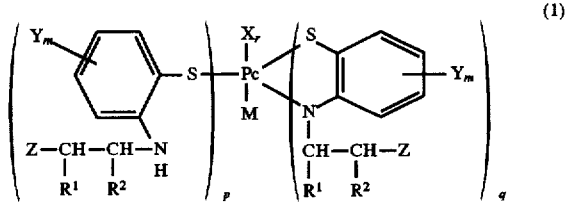

(1)

wherein $R^1$ and $R^2$ each independently represents a hydrogen atom, a substituted or unsubstituted alkyl group or a substituted or unsubstituted aryl group; Ys each independently represents a substituted or unsubstituted alkyl group, a substituted or unsubstituted aryl group, a substituted or unsubstituted alkoxy group, or a substituted or unsubstituted aryloxy group; m stands for an integer of 0 to 4; Pc represents a phthalocyanine nucleus; S represents an —SH group or an —NHR$^3$ group in which R$^3$ represents a hydrogen atom, a substituted or unsubstituted alkyl group or a substituted or unsubstituted aryl group; Xs each independently represents a halogen atom, a hydroxy group, a substituted or unsubstituted alkoxy group, a substituted or unsubstituted aryloxy group, a substituted or unsubstituted alkylthio group, a substituted or unsubstituted arylthio group, a substituted or unsubstituted alkylamino group, a substituted or unsubstituted arylamino group and a substituted or unsubstituted alkylarylamino group; the adjacent pairs of Xs may form a 5- or 6-membered ring via two hereto atoms; M represents a divalent metal atom, a substituted trivalent or tetravalent metal or an oxymetal atom; p stands for an integer of 1 to 16; q stands for an integer of 0 to 8; r stands for an integer of 0 to 8; and p+2q+r is not greater than 16.

In a further aspect of this invention, there is also provided a process for the preparation of the phthalocyanine near infrared absorber of formula (1) having a broad absorption range in the near infrared region, which comprises reacting in the presence of a base a phthalocyanine represented by the following formula (2):

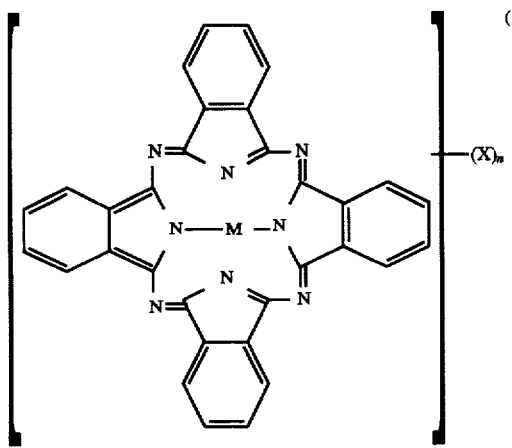

(2)

wherein Xs each independently represents a halogen atom, a hydroxy group, a substituted or unsubstituted alkoxy group, a substituted or unsubstituted aryloxy group, a substituted or unsubstituted alkylthio group, a substituted or unsubstituted arylthio group, a substituted or unsubstituted alkylamino group, a substituted or unsubstituted arylamino group and a substituted or unsubstituted alkylarylamino group; the adjacent pairs of Xs may form a 5- or 6-membered ring via two hetero atoms; M represents a divalent metal atom, a substituted trivalent or tetravalent metal or an oxymetal atom, n stands for an integer of 4 to 16, with the proviso that at least four of the Xs each represents a halogen atom, with at least one 2-aminothiophenol derivative represented by the following formula (3):

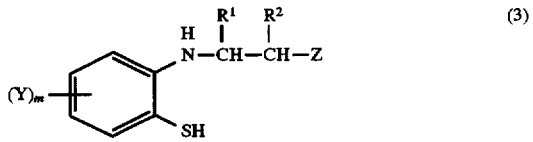

(3)

wherein $R^1$ and $R^2$ each independently represents a hydrogen atom, a substituted or unsubstituted alkyl group or a substituted or unsubstituted aryl group; Ys each independently represents a substituted or unsubstituted alkyl group, a substituted or unsubstituted aryl group, a substituted or unsubstituted alkoxy group, or a substituted or unsubstituted aryloxy group; Z represents an —SH group or an —NHR$^3$ group in which R$^3$ represents a hydrogen atom, a substituted or unsubstituted alkyl group or a substituted or unsubstituted aryl group; and m stands for an integer of 0 to 4.

In a still further aspect of the invention, there are also provided a near infrared absorbing resin composition and heat-ray absorbing filter each comprising the near infrared absorber represented by the above formula (1).

The present invention has made it possible to easily provide a phthalocyanine near infrared absorber which has high light fastness, high solubility and a wide absorption range in the near infrared region of from 700 to 1,800 nm and is useful for the production of near infrared absorbing resin compositions and heat-ray absorbing films. The present invention is therefore extremely valuable from a practical standpoint.

DETAILED DESCRIPTION OF THE PREFERRED EMBODIMENTS

Figure 1:
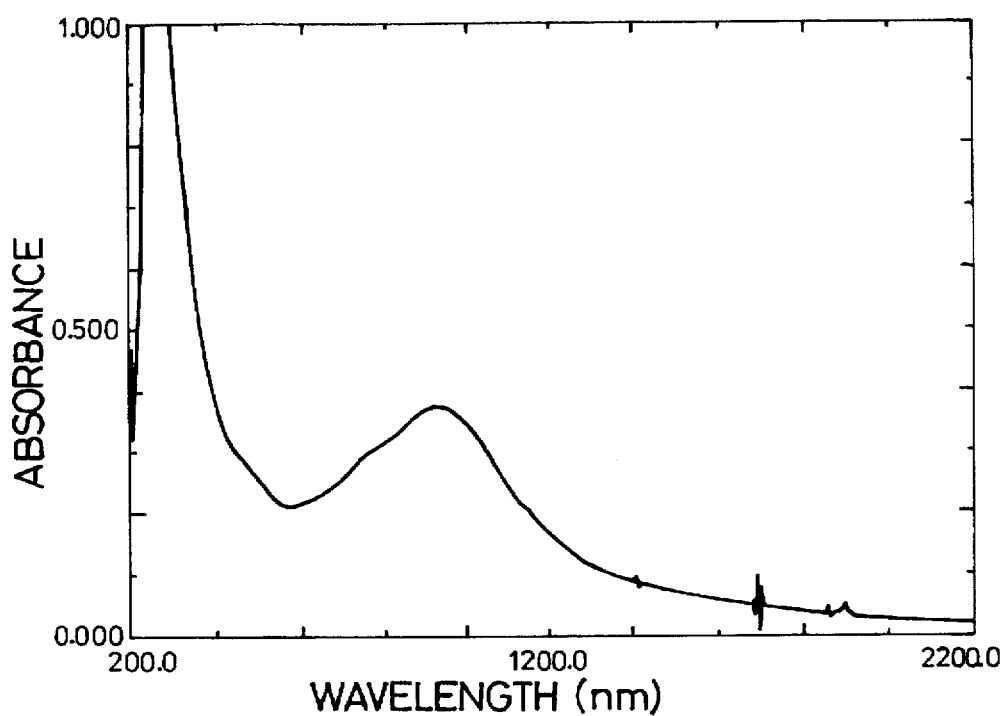
FIGS. 1, 2 and 3 are absorption spectra of near infrared absorbing mixture obtained in Examples 1, 2 and 3, respectively.

The present invention will next be described in detail.

The near infrared absorber according to the present invention is a phthalocyanine near infrared absorber which is represented by formula (1) and has a broad absorption range in the near infrared region.

In formula (1), the substituted or unsubstituted alkyl group represented by $R^1$ or $R^2$, or $R^3$ in Z is a substituted or unsubstituted $C_{1-20}$ alkyl group. Examples include methyl, ethyl, n-propyl, iso-propyl, n-butyl, iso-butyl, sec-butyl, n-pentyl, iso-pentyl, 1,2-dimethylpropyl, n-hexyl, 1,3-dimethylbutyl, 1,2-dimethylbutyl, n-heptyl, 1,4-dimethylpentyl, 1-ethyl-3-methylbutyl, n-octyl, 2-ethylhexyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-eicosyl, benzyl, sec-phenylethyl, 2-methylbenzyl, 3-methylbenzyl, 4-methylbenzyl and 2-phenylethyl.

The substituted or unsubstituted aryl group is a $C_{6-20}$ substituted or unsubstituted aryl group. Examples include phenyl, 2-mercaptophenyl, 3-mercaptophenyl, 4-mercaptophenyl, 2-methylphenyl, 3-methylphenyl, 4-methylphenyl and naphthyl. Preferred examples of the substituent represented by $R^1$ and $R^2$ include methyl, ethyl, n-propyl, iso-propyl, n-butyl, iso-butyl, sec-butyl, n-pentyl, iso-pentyl, 1,2-dimethylpropyl, n-hexyl, 1,3-dimethylbutyl, 1,2-dimethylbutyl, n-heptyl, 1,4-dimethylpentyl, 1-ethyl-3-methylbutyl, n-octyl, 2-ethylhexyl, n-nonyl, n-decyl, and phenyl.

Examples of the substituent represented by Z include groups SH and $NHR^3$, with $NHR^3$ being particularly preferred. Preferred examples of $R^3$ include substituted or unsubstituted $C_{6-20}$ aryl groups such as phenyl, 2-mercaptophenyl, 3-mercaptophenyl, 4-mercaptophenyl, 2-methylphenyl, 3-methylphenyl, 4-methylphenyl and naphthyl.

The substituted or unsubstituted alkyl group represented by Y is a substituted or unsubstituted $C_{1-20}$ alkyl group. Specific examples include methyl, ethyl, n-propyl, isopropyl, n-butyl, iso-butyl, sec-butyl and t-butyl. The substituted or unsubstituted aryl group is a substituted or unsubstituted $C_{6-20}$ aryl group. Specific examples include phenyl, 2-methylphenyl, 3-methylphenyl, 4-methylphenyl and naphthyl. The substituted or unsubstituted alkoxy group is a substituted or unsubstituted $C_{1-20}$ alkoxy group. Examples include methoxy, ethoxy, n-propoxy, iso-propoxy, n-butoxy, iso-butoxy and sec-butoxy. The substituted or unsubstituted aryloxy group is a substituted or unsubstituted $C_{6-20}$ aryloxy group. Examples include phenoxy, 2-methylphenoxy, 3-methylphenoxy, 4-methylphenoxy and naphthoxy.

Exemplary halogen atoms represented by X are fluorine, chlorine, bromine and iodine. No particular limitation is imposed on the substituted or unsubstituted alkoxy group represented by X, however, examples include methoxy, ethoxy, n-propoxy, iso-propoxy, n-butoxy, iso-butoxy, sec-butoxy, n-pentoxy, iso-pentoxy, n-hexyloxy, cyclohexyloxy, n-heptyloxy, n-octyloxy, 2-ethylhexyloxy, n-nonyloxy, methoxyethoxy, ethoxyethoxy, ethoxyethoxyethoxy, hydroxyethoxyethoxy, diethylaminoethoxy and benzyloxy.

No particular limitation is imposed on the substituted or unsubstituted aryloxy group represented by X, however, examples include phenoxy, 2-methylphenoxy, 3-methylphenoxy, 4-methylphenoxy and naphthoxy.

No particular limitation is imposed on the substituted or unsubstituted alkylthio group represented by X, however, examples include unsubstituted alkylthio groups such as methylthio, ethylthio, n-propylthio, iso-propylthio, n-butylthio, iso-butylthio, sec-butylthio, t-butylthio, n-pentylthio, iso-pentylthio, neo-pentylthio, n-hexylthio, cyclohexylthio, n-heptylthio, n-octylthio and n-nonylthio; alkylalkylthio groups such as 1,2-dimethyl-propylthio and 2-ethylhexylthio; alkoxyalkylthio groups such as methoxymethylthio, methoxyethylthio, ethoxyethylthio, propoxyethylthio, butoxyethylthio, γ-methoxypropylthio, γ-ethoxypropylthio, dimethoxymethylthio, diethoxymethylthio, dimethoxyethylthio and diethoxyethylthio; alkoxyalkoxyalkylthio groups such as methoxyethoxyethylthio and ethoxyethoxyethylthio; alkoxyalkoxyalkoxyalkylthio groups; halogenated alkylthio groups such as chloromethylthio; monoalkylaminoalkylthio groups; and dialkylaminoalkylthio groups such as dimethylaminoethylthio and diethylaminoethylthio.

No particular limitation is imposed on the substituted or unsubstituted arylthio group represented by X, however, examples include phenylthio, naphthylthio, 4-methylphenylthio, 4-ethylphenylthio, 4-propylphenylthio, 4-t-butylphenylthio, 4-methoxyphenylthio, 4-ethoxyphenylthio, 4-aminophenylthio, 4-alkylaminophenylthio, 4-dialkylaminophenylthio, 4-phenylaminophenylthio, 4-diphenylaminophenylthio, 4-hydroxyphenylthio, 4-chlorophenylthio, 4-bromophenylthio, 2-methylphenylthio, 2-ethylphenylthio, 2-propylphenylthio, 2-t-butylphenylthio, 2-methoxyphenylthio, 2-ethoxyphenylthio, 2-aminophenylthio, 2-alkylaminophenylthio, 2-dialkylaminophenylthio, 2-phenylaminophenylthio, 2-diphenylaminophenylthio, 2-hydroxyphenylthio, 2-chlorophenylthio and 2-bromophenylthio.

No particular limitation is imposed on the substituted or unsubstituted alkylamino group represented by X, however, examples include methylamino, ethylamino, n-propylamino, iso-propylamino, butylamino, pentylamino, dipentylamino, hexylamino, heptylamino, octylamino, nonylamino and benzylamino.

No particular limitation is imposed on the substituted or unsubstituted arylamino group represented by X, however, examples include phenylamino, alkylphenylamino, alkoxyphenylamino, hydroxyphenylamino and naphthylamino.

Illustrative examples of the substituent in which adjacent pairs of Xs form a 5- or 6-membered ring via two hetero atoms include substituents represented by the following formulas:

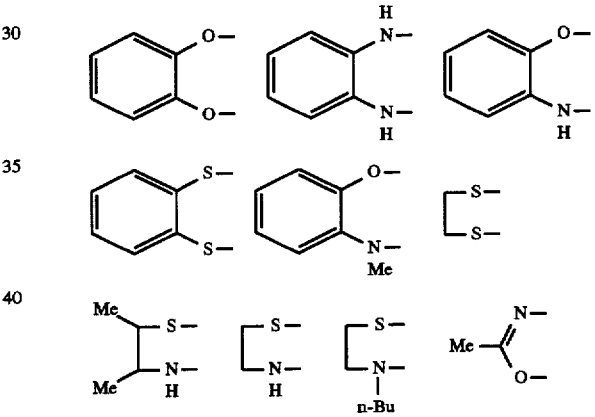

Examples of the divalent metal represented by M include Cu(II), Zn(II), Fe(II), Co(II), Ni(II), Ru(II), Rh(II), Pd(II), Pt(II), Mn(II), Mg(II), Ti(II), Be(II), Ca(II), Ba(II), Cd(II), Hg(II), Pb(II) and Sn(II).

Illustrative examples of the monosubstituted trivalent metal include Al-Cl, Al-Br, Al-F, Ai-I, Ga-Cl, Ga-F, Ga-I, Ga-Br, In-Cl, In-Br, In-I, In-F, Tl-Cl, Tl-Br, Tl-I, Tl-F, Al-$C_6H_5$, Al-$C_6H_4(CH_3)$, In-$C_6H_5$, In-$C_6H_4(CH_3)$, Mn(OH), Mn($OC_6H_5$), Mn[$OSi(CH_3)_3$], Fe-Cl and Ru-Cl.

Examples of the disubstituted tetravalent metal include $CrCl_2$, $SiCl_2$, $SiBr_2$, $SiF_2$, $SiI_2$, $ZrCl_2$, $GeCl_2$, $GeBr_2$, $GeI_2$, $GeF_2$, $SnCl_2$, $SnBr_2$, $SnF_2$, $TiCl_2$, $TiBr_2$, $TiF_2$, $Si(OH)_2$, $Ge(OH)_2$, $Sn(OH)_2$, $Zr(OH)_2$, and $Mn(OH)_2$; $TiR_2$, $CrR_2$, $SiR_2$, $SnR_2$ and $GeR_2$ in which R represents an alkyl, phenyl or naphthyl group or a derivative thereof; $Si(OR')_2$, $Sn(OR')_2$, $Ge(OR')_2$, $Ti(OR')_2$ and $Cr(OR')_2$ in which R' represents an alkyl, phenyl, naphthyl, trialkylsilyl or dialkylalkoxysilyl group or a derivative thereof; $Sn(SR")_2$ and $Ge(SR")_2$ in which R" represents an alkyl, phenyl or naphthyl group or a derivative thereof.

Exemplary oxymetals include VO, MnO and TiO.

Particularly preferred examples of M include Cu, AlCl, TiO and VO, with Cu being still more preferred.

The subscript "p" stands for an integer of 1 to 16, with 4 to 12 being particularly preferred. The subscript "q" stands for an integer of 0 to 8, with 1 to 4 being particularly preferred. The subscript "r" stands for an integer of 0 to 8, with 0 to 4 being particularly preferred. These p, q and r are required to satisfy the formula: "p+2q+r≦16". Among such p, q and r, greater p or q can provide a broader absorption range. Particularly, the greater q the more preferred.

The phthalocyanine near infrared absorber according to the present invention can be prepared easily by reacting a phthalocyanine, which contains eliminative groups or atoms such as halogen atoms, with 2-aminothiophenol derivative. Specifically, the process according to the present invention for the preparation of the phthalocyanine near infrared absorber comprises reacting, in the presence of a base, a phthalocyanine represented by the following formula (2):

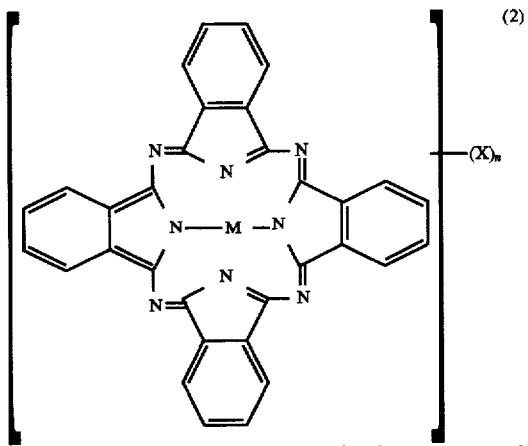

(2)

with at least one 2-aminothiophenol derivative represented by the following formula (3):

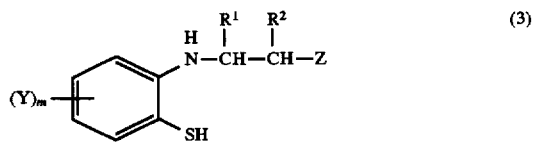

(3)

In the above formulas, $R^1$, $R^2$, X, Y, Z, M, m and n have the same meanings as defined above.

In general, introduction of one or more amino groups onto at least one of the benzene rings of phthalocyanine makes it possible to achieve an absorption of longer wavelengths in a broader range. An amino-containing compound, however, has poor reactivity so that it does not readily react with the phthalocyanine of formula (2). In the present invention, the compound containing both thiol and amino moieties is employed. The phthalocyanine of formula (2) is first reacted with the thiol moiety having higher reactivity, followed by the induction of intramolecular cyclization to introduce the amino moiety therein. As a result of the intramolecular cyclization, a stable 6-membered ring structure can be formed through the sulfur atom and the nitrogen atom so that a product having strong light fastness can be obtained.

In the phthalocyanine represented by formula (2) which is used in the present invention, the substituent represented by X has the same meaning as defined in formula (1). The subscript "n" stands for an integer of 4 to 16, with 8 to 16 being particularly preferred. To cause the nucleophilic substituting reaction smoothly, X should excellently act as an eliminative group. Accordingly, at least four of the Xs are halogen atoms.

As to the availability of the phthalocyanine, those containing chlorine and/or bromine atoms as Xs are industrially available. Those containing iodine atoms as Xs can be obtained by treating these industrially-available phthalocyanines with potassium iodide, sodium iodide or the like in a manner known per se in the art to substitute the chlorine and/or bromine atoms by a like number of iodine atoms. A fluorinated phthalocyanine can be prepared from a commercially available fluorinated phthalonitrile in accordance with the process disclosed in "Dye and Pigment", 91 (1992). A phthalocyanine containing substituents X other than halogen atoms, on the other hand, can be prepared by reacting a corresponding halogenated phthalocyanine with any one of mercaptans, alcohols, amines and the like to cause partial substitution; or alternatively, by using as a starting material 2,3-dicyano-5,6-dichloroquinone (DDQ) as disclosed in Japanese Patent Laid-Open No. 62878/1991.

Particularly preferred examples of the phthalocyanine represented by formula (2) include C.I. Pigment Green 7 ("Phthalocyanine Green", trade name), C.I. Pigment Green 36, C.I. Pigment Green 37 and C.I. Pigment Green 38. They are compounds easily available as halogenated phthalocyanines in industry.

In formula (2), M has the same meaning as defined in formula (1). Particularly preferred are Cu, AlCl, TiO and VO, with Cu being more preferred.

In the 2-aminothiophenol derivative which is represented by formula (3) and is useful in the practice of this invention, Y, m, $R^1$, $R^2$ and Z have the same meanings as defined in formula (1). Preferred is a compound represented by the following formula (4):

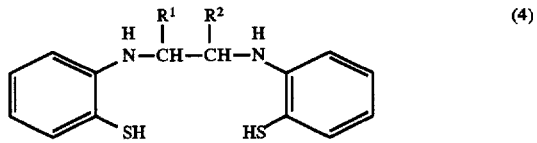

(4)

wherein $R^1$ and $R^2$ have the same meanings as defined in formula (1).

The compound may be in the form of a salt with a metal such as zinc, mercury, cadmium, iron (II) or nickel. In particular, the compound of formula (4) becomes stable when formed into a salt with zinc and moreover, upon reaction in the presence of a base, the salt releases zinc readily and the residue reacts with the compound of formula (2).

The 2-aminothiophenol derivative usable in the present invention can be obtained usually by any one of the processes disclosed in "Synthesis", 288 (1985), Chem. Ber., 101, 1579 (1968), Can. J. Chem., 52, 1054 (1974) and the like. For example, it can be prepared easily by reacting a corresponding aldehyde or ketone with 2-aminothiophenol and then subjecting the reaction product to reduction.

The reaction between the phthalocyanine of formula (2) and the 2-aminothiophenol derivative of formula (3) can be conducted under conditions generally adapted for nucleophilic substituting reactions, specifically, in the presence of a base such as sodium hydroxide, potassium hydroxide, sodium carbonate, potassium carbonate or sodium hydride.

This reaction may also be conducted in the presence of a solvent. Exemplary solvents in this case include polar solvents such as dimethyl formamide (DMF), dimethyl sulfoxide (DMSO), 1,3-dimethyl-2-imidazolidinone (DMI) and sulfolane; ketone solvents such as acetone and methyl ethyl ketone; and aromatic hydrocarbon solvents such as toluene, xylene, monochlorobenzene and dichlorobenzene.

The near infrared absorbing compound according to the present invention can usually be prepared by dissolving or suspending the phthalocyanine of formula (2) and a base (in an amount of 4 to 100 times, preferably 5 to 50 times as much as the equivalent of the phthalocyanine) in a solvent (in an amount of 1 to 1,000 times as much as the weight of the phthalocyanine), adding the 2-aminothiophenol derivative of formula (3) (in an amount of 1 to 30 times, preferably 2 to 10 times as much as the equivalent of the phthalocyanine) under stirring to the resulting solution or suspension and then reacting them at 50° to 220° C. The addition of the 2-aminothiophenol derivative can be performed either before, during or after heating. It can be added either at once or in portions. Alternatively, it is also possible to use the 2-aminothiophenol derivative itself as a solvent and subsequent to addition of a base, to add the phthalocyanine.

The reaction can also be performed as needed by using in combination two or more 2-aminothiophenol derivatives described herein or adding a substituted or unsubstituted phenol, a substituted or unsubstituted thiophenol, or a reactive-substituent-containing compound such as 2-aminothiophenol or a 2-alkylaminothiophenol concurrently with the 2-aminothiophenol derivative.

Upon the reaction, a copper catalyst such as metal copper, copper chloride, copper bromide, copper iodide or copper oxide can be added to accelerate the reaction. The reaction can be conducted either at normal pressure or under elevated pressure.

According to the reaction in the present invention, the phthalocyanine near infrared absorber of formula (1) is obtained as a main product, which is a mixture of products obtained by a reaction of the 2-aminothiophenol derivative of formula (3) at one site, namely, at the mercapto group thereof with the phthalocyanine of formula (2) and/or a reaction of the 2-aminothiophenol derivative of formula (3) at two site, namely, at the mercapto and amino groups thereof with the phthalocyanine. Moreover, the mixture may also contain products obtained by further reacting the 2-aminothiophenol derivative at group Z with the phthalocyanine in addition to the above two site.

The progress of the reaction can be determined, for example, by measuring the $\lambda_{max}$ of the reaction mixture.

After the completion of the reaction, the reaction mixture is poured into cooled water or an alcohol such as methanol, ethanol, propanol, butanol or pentanol to precipitate the target compounds. The compounds so precipitated are separated by suction filtration, successively washed with water and an alcohol to remove the salt, remaining base, unreacted 2-aminothiophenol derivative and the like, and then dried, whereby the near infrared absorber of the present invention can be separated. The near infrared absorber of the present invention so obtained is highly soluble in an organic solvent such as chloroform, toluene, xylene or ethyl acetate so that it can be further purified by column chromatography as needed.

Any unreacted mercapto or amino group in the near infrared absorber prepared according to the present process can be alkylated by reacting the absorber with an alkyl halide such as a methyl halide, ethyl halide, 1-halopropane, 2-halopropane, 1-halobutane, 2-halobutane, 1-halo-2-methylbutane, 1-halo-3-methylbutane, 1-halopentane, 1-halohexane, 1-halo-2-ethylhexane, 1-haloheptane, 1-halooctane, 1-halononane, 1-halodecane or benzyl halide under the same conditions as described above. As the halogen atom, a chlorine, bromine or iodine atom can be used.

In this case, the near infrared absorber, which has been isolated as described above, and a base (in an amount of 1 to 100 times as much as the weight of the near infrared absorber) are dissolved or suspended in a solvent (in an amount of 1 to 1,000 times as much as the weight of the near infrared absorber). To the resulting solution or suspension, the alkyl halide (in an amount of 1 to 100 times as much as the weight of the near infrared absorber) is added under stirring to conduct alkylation at 50° to 220° C.

Alternatively, the alkyl halide can be added directly to the reaction mixture of the phthalocyanine and the 2-aminothiophenol derivative without isolating the near infrared absorber and the alkylation can then be effected under heat.

After the completion of the alkylation, the reaction mixture can be treated similarly as described above.

The near infrared absorber according to the present invention can be formulated into a near infrared absorbing resin composition by kneading it under heat with a resin such as polyethylene, polypropylene, polyvinyl chloride, polystyrene, melamine, polyurethane, polyether, polycarbonate, polyester, polyacrylate, polymethacrylate, polyvinylbutyral or ethylene-vinyl acetate copolymer; or by dissolving a mixture of the absorber and the resin in an organic solvent such as chloroform, toluene, xylene, acetone, methyl ethyl ketone (MEK), ethyl acetate, butyl acetate, dibutyl ether or dimethylformamide (DMF). The resin composition so obtained can be used as a near infrared absorbing ink or coating formulation.

A photosetting near infrared absorbing resin composition can be obtained by mixing the near infrared absorber and a photoreactive monomer or oligomer together with a photopolymerization catalyst. The resin composition so obtained can also be used as a near infrared absorbing ink and coating formulation as above.

The above kneaded resin mixture can be formed into a resin plate; or extruded and stretched into a film as a heat-ray absorbing filter.

In addition, the above near infrared absorbing ink or coating formulation can be applied onto a glass plate or a transparent resin film or plate such as a polyester, polymethacrylate, polyvinyl chloride or polycarbonate film or plate. Moreover, the near infrared absorber can be kneaded in an adhesive for glass such as polyvinyl butyral to fabricate a laminated glass which can be used as a heat-ray absorbing laminated glass.

The process according to the present invention for the preparation of the near infrared absorber makes it possible to use an inexpensive pigment as a starting material and to easily obtain a compound which has an absorption in a longer wavelength range, high light fastness and high solubility in a resin, solvent or the like. In addition, the product available according to the process of the present invention is not in the form of a single compound but a mixture of several compounds, thereby making it possible to absorb broader wavelengths and moreover, a wide range of near infrared rays. These advantages make it easy to apply the product to near infrared absorbing filters or the like. Accordingly, the product is excellent for the absorption of heat rays.

The present invention will next be described more specifically by the following examples. It should however be borne in mind that this invention is by no means limited to or by the examples.

EXAMPLE 1

In 200 ml of 1,3-dimethyl-2-imidazolidinone (DMI), 10.0 g (8.87 mmol) of C.I. Pigment Green 7 ("Phthalocyanine Green", trade name), 16.3 g (44.35 mmol, 5 times equivalent) of a zinc complex of a 2-aminothiophenol derivative represented by the following formula (6):

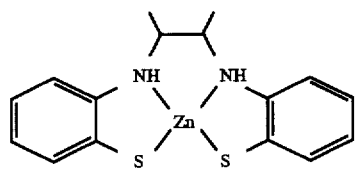
(6)

and 39.2 g (283.63 mmol, 32 times equivalent) of potassium carbonate were reacted at 170° C. for 2 hours. The reaction mixture was allowed to cool down to room temperature and was then poured into 500 ml of methanol. The resulting precipitate was collected by suction filtration, washed successively with methanol and water and then dried, whereby 14.5 g of a near infrared absorber containing a compound represented by the following formula (7):

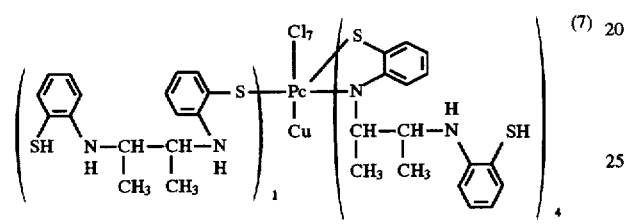
(7)

were obtained.

An absorption spectrum of the resulting mixture in chloroform is shown in FIG. 1. As is apparent from the figure, the absorber has an absorption peak broader than the conventional phthalocyanine and absorbs the near infrared rays of 700 to 1,800 nm well. In particular, a marked difference is observed in the absorption in a range not shorter than 1,000 nm (see Comparative Examples).

EXAMPLE 2

In a similar manner to Example 1 except that 8.8 g (26.61 mmol, 3 times equivalent) of a 2-aminothiophenol derivative represented by the following formula (8):

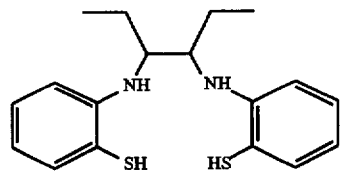
(8)

and 12.6 g (53.22 mmol, 6 times equivalent) of 2-(n-octylaminothiophenol were used instead of the 2-aminothiophenol derivative zinc complex of formula (6), a reaction was conducted. The reaction mixture was subjected to post treatments as in Example 1, whereby 13.7 g of a near infrared absorber containing a compound represented by the following formula (9):

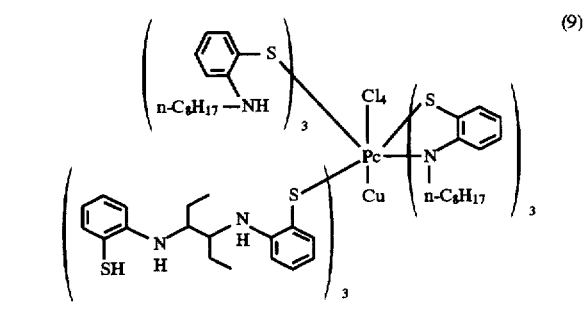
(9)

were obtained.

Figure 2:
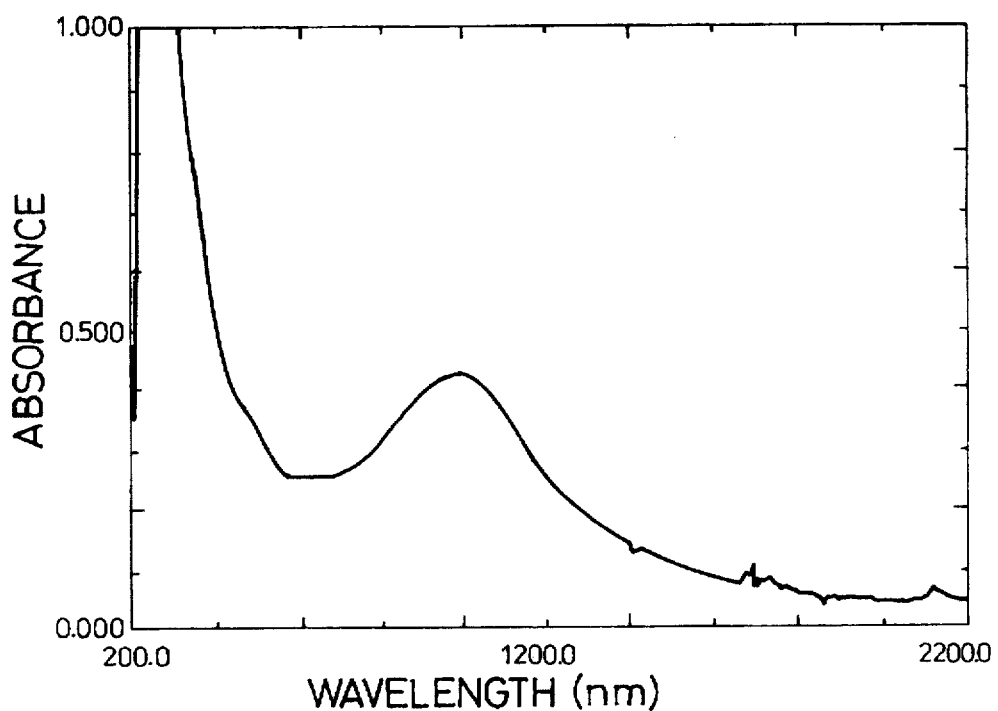

An absorption spectrum of the resulting mixture in chloroform is shown in FIG. 2. As is apparent from the figure, the absorber has an absorption peak broader than the conventional phthalocyanine and absorbs the near infrared rays of 700 to 1,800 nm well. In particular, a marked difference is observed in the absorption in a range not shorter than 1,000 nm (see Comparative Examples).

EXAMPLE 3

In a similar manner to Example 1 except that 27.6 g (79.83 mmol, 9 times equivalent) of a 2-aminothiophenol derivative represented by the following formula (10):

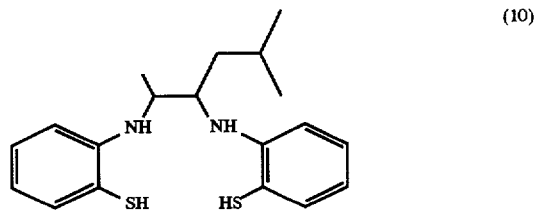
(10)

were used instead of the 2-aminothiophenol derivative zinc complex of formula (6), a reaction was conducted. The reaction mixture was subjected to post treatments as in Example 1, whereby 19.2 g of a near infrared absorber containing a compound represented by the following formula (11):

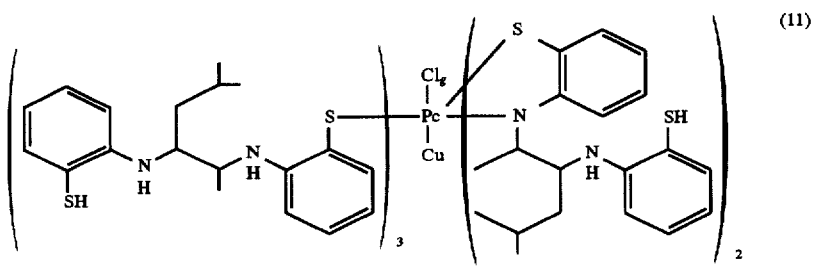
(11)

were obtained.

Figure 3:
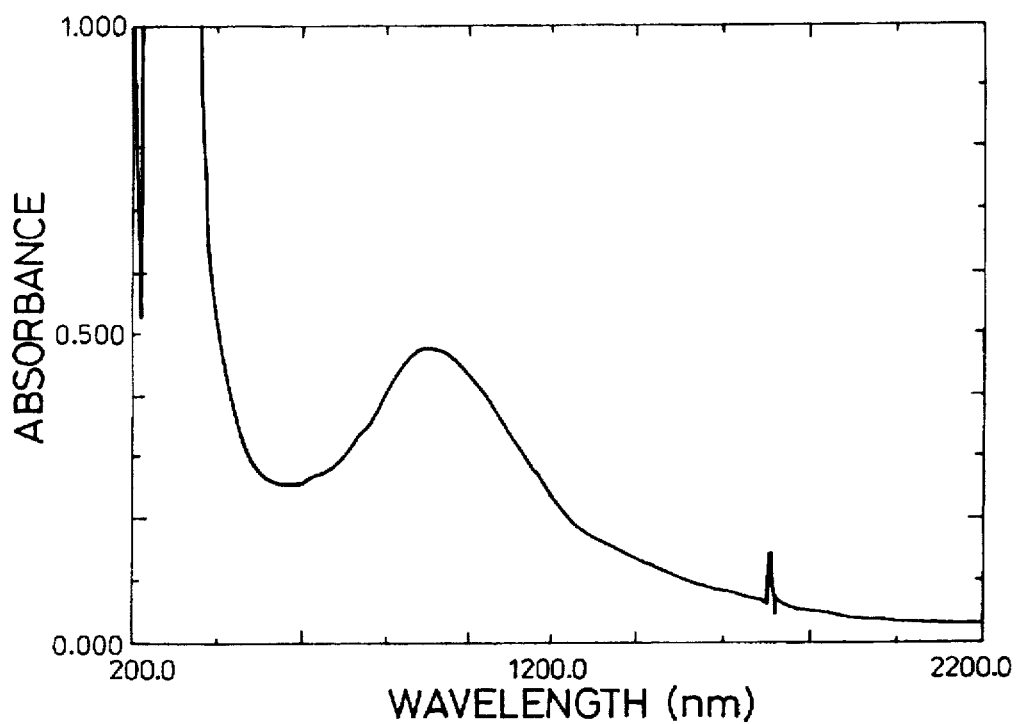

An absorption spectrum of the resulting mixture in chloroform is shown in FIG. 3. As is apparent from the figure, the absorber has an absorption peak broader than the conventional phthalocyanine and absorbs the near infrared rays of 700 to 1,800 nm well. In particular, a marked difference is observed in the absorption in a range not shorter than 1,000 nm (see Comparative Examples).

EXAMPLE 4

In a similar manner to Example 1 except that the amount of the 2-aminothiophenol derivative zinc complex of formula (6) was increased by three times (48.9 g, 133.05 mmol, 15 times equivalent), 25.3 g of a near infrared absorber containing a compound represented by the following formula (12):

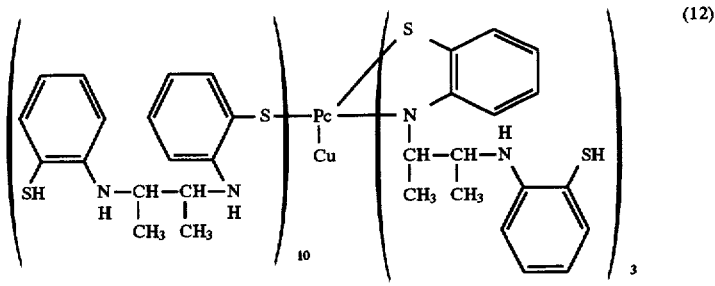

were obtained. The absorber has an absorption peak broader than the conventional phthalocyanine and absorbs the near infrared rays of 700 to 1,800 nm well.

EXAMPLE 5

In a similar manner to Example 1 except that 44.0 g (133.05 mmol, 15 times equivalent) of the compound of formula (8), which had been employed in Example 2, were used instead of the 2-aminothiophenol derivative zinc complex of formula (6), whereby 35.3 g of a near infrared absorber containing a compound represented by the following formula (13):

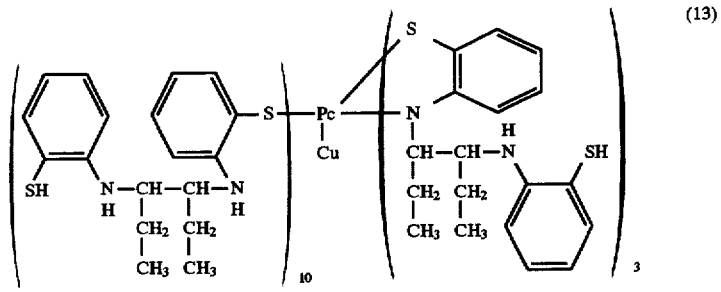

were obtained. The absorber has an absorption peak broader than the conventional phthalocyanine and absorbs the near infrared rays of 700 to 1,800 nm well.

EXAMPLE 6

Figure 4:
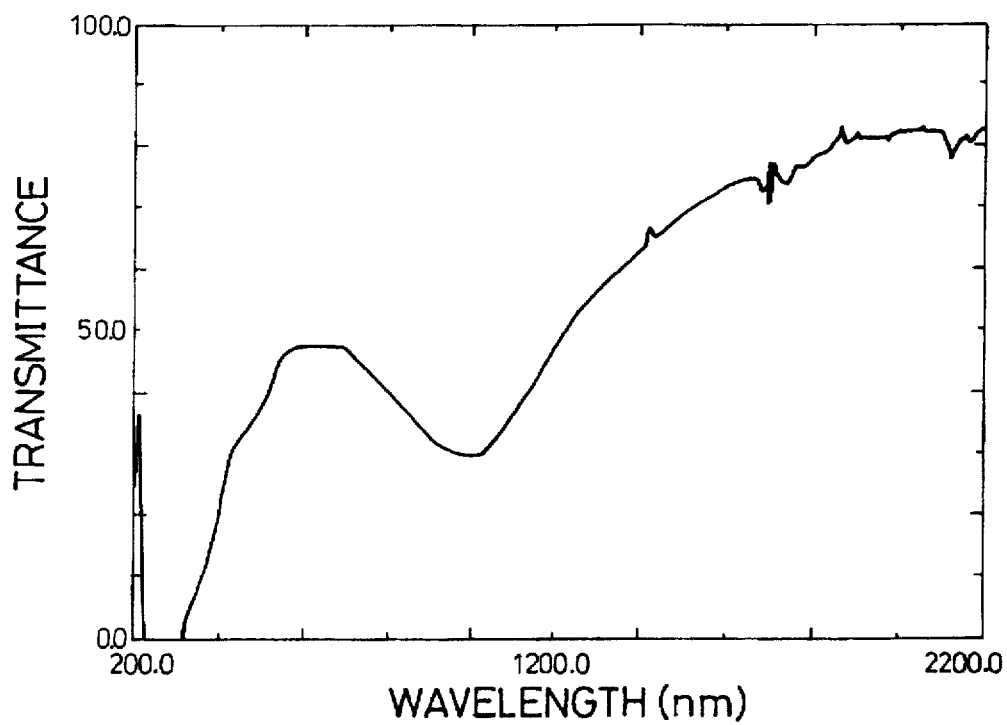
FIGS. 4 and 5 are transmittance spectra of heat-ray absorbing films obtained in Examples 6 and 7, respectively.

The near infrared absorber, which had been prepared in Example 1, was mixed with a polyethylene terephthalate pellet No. 1203 (product of Unichika, Ltd.) at a weight ratio of 0.03:1, followed by melting at 260°–280° C. The melt so obtained was formed into a film of 100 μm in thickness by an extruder. The film so obtained was biaxially oriented to produce a heat-ray absorbing film of 25 μm in thickness. A transmittance spectrum of the resulting film is shown in FIG. 4. As is apparent from the figure, the film has a broader absorption peak than a heat-ray absorbing film obtained in the same manner as above except for using the conventional phthalocyanine and absorbs the near infrared rays of 700 to 1,800 nm well. In particular, a marked difference is observed in the absorption range not shorter than 1,000 nm (See Comparative Example 3).

A light fastness test was conducted at 63° C. for 300 hours on the film under a carbon arc lamp. As a result, no reduction in absorption due to the decomposition of the pigment was observed, thereby demonstrating good light fastness.

EXAMPLE 7

Figure 5:
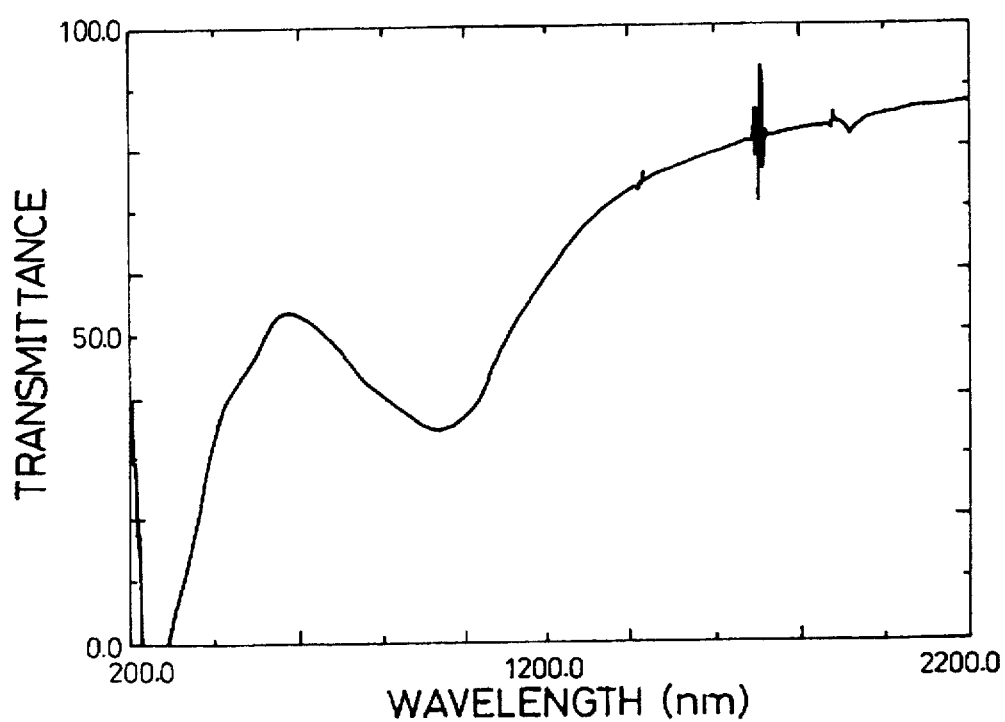

In 30 g of a 1:1 mixed solvent of toluene and methyl ethyl ketone (MEK), 0.4 g of the near infrared absorber, which had been prepared in Example 2, and 5 g of polymethyl methacrylate (PMMA) pellets ("Delpet 80N", trade name; product of Asahi Chemical Industry Co., Ltd.) were dissolved to prepare a near infrared absorbing coating formulation. The coating formulation so obtained was applied onto a PET film ("Lumilar", trade name; product of Toray Industries, Inc.) by a coil bar, followed by drying at room temperature for one hour to remove the solvent so that a heat-ray absorbing film was produced. A transmittance spectrum of the resulting film is shown in FIG. 5. As is apparent from the figure, the film has a broader absorption peak than a heat-ray absorbing film obtained in the same manner as above except for using the conventional phthalocyanine and absorbs the near infrared rays of 700 to 1,800 nm well. In particular, a marked difference is observed in the absorption range not shorter than 1,000 nm (See Comparative Example 5).

A light fastness test was conducted at 63° C. for 300 hours on the film under a carbon arc lamp. As a result, no reduction in absorption due to the decomposition of the pigment was observed, thereby demonstrating good light fastness.

EXAMPLE 8

Mixed were 5 g of the near infrared absorber prepared in Example 1, 2,000 g of a polyvinyl butyral adhesive ("Eslec Film", trade name; product of Sekisui Chemical Co., Ltd.) and 10 g of an ultraviolet absorber ("Tinuvin P.", trade mark; product of CIBA-GEIGY AG), followed by melting at 200°–240° C. The melt so obtained was formed into a film of 300 μm in thickness by an extruder. The film was put between two sheets of float glass, each having a 3 mm thickness, followed by treating at 130° C. and 12 kg/cm² for 20 minutes in an autoclave, whereby a laminated glass was produced. The laminated glass so obtained absorbed the near infrared rays of 700–1,800 run well.

A light fastness test was conducted on the laminated glass at 63° C. for 300 hours under a carbon arc lamp. As a result, no reduction in absorption due to the decomposition of the pigment was observed, thereby demonstrating good light fastness.

EXAMPLE 9

In 5 g of an acrylate monomer ("Light Acrylate BP-4EA", trade name; product of Kyoeisha Chemical Co., Ltd.), 0.2 g of the near infrared absorber prepared in Example 1 and 0.2 g of a photopolymerization catalyst ("Kayacure DEXT", trade name; product of NIPPON KAYAKU CO., LTD.) were dissolved, whereby a photosetting resin composition was prepared as a coating formulation. By using a coil bar, the composition was applied onto a transparent PET film ("Lumilar", trade name; product of Toray Industries, Inc.) and a white PET film ("Lumilar" white type, trade name; product of Toray Industries, Inc.), respectively. The films so coated were exposed to-light at 400 mJ/cm² under a high pressure mercury lamp ("Rapidcure", trade name; exposure apparatus manufactured by Ushio Inc.) so that they were cured. As a result of measurement of a transmittance and reflectivity spectrum of each of the resulting films, each film was found to have good absorbance of the near infrared rays of 700 to 1,800 nm.

A light fastness test was conducted on these films at 63° C. for 300 hours under a carbon arc lamp. As a result, no reduction in absorption due to the decomposition of the pigment was observed, thereby demonstrating good light fastness.

EXAMPLE 10

In 20 ml of DMF, 1.0 g of the near infrared absorber obtained in Example 1, 3.9 g (28.22 mmol) of potassium carbonate and 3.0 g (14.09 mmol) of 1-iodohexane were reacted at 120° C. for 3 hours. After the reaction mixture was allowed to cool down to room temperature, it was poured into 100 g of methanol. The resulting precipitate was collected by suction filtration, washed successively with methanol and water, and then dried, whereby 1.1 g of a near infrared absorber mixture were obtained.

The resulting mixture had a broad absorption spectrum and showed good absorption of the near infrared rays of 700 to 1,800 nm.

EXAMPLE 11

In 200 ml of DMF, 10.0 g of C.I. Pigment Green 38, 10.1 g (44.35 mmol) of a 2-aminothiophenol derivative represented by the following formula (14):

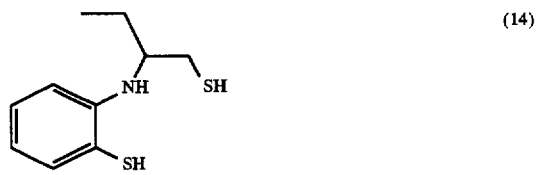

(14)

0.5 g of cuprous chloride and 39.2 g (283.63 mmol) of potassium carbonate were reacted at 120° C. for 3 hours. After the reaction mixture was allowed to cool down to room temperature, it was poured into 500 ml of water. The resulting precipitate was collected by suction filtration, washed successively with methanol and water and then dried, whereby 1.1 g of a near infrared absorber containing a compound represented by the following formula (15):

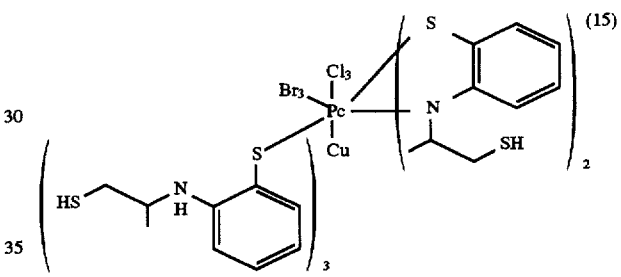

(15)

were obtained.

The absorber so obtained had a broad absorption spectrum and showed significant absorption of the near infrared rays of 700 to 1,800 nm.

EXAMPLES 12–20

In each Example, a reaction between the corresponding phthalocyanine and aminothiophenol derivative shown in Table 1 was conducted in a similar manner to Example 4. The results are also shown in Table 1. The near infrared absorbers, subsequent to isolation, each had a broad absorption and showed significant absorption of the near infrared rays of 700 to 1,800 nm.

TABLE 1

| Example | Raw material phthalocyanine | Aminothiophenol derivative | Maximum absorption (nm) |
| --- | --- | --- | --- |
| 12 | (vanadyl hexadecafluorophthalocyanine structure) | (2-methyl-6-(1-methylpropyl-thiomethyl)aminothiophenol structure) | 1050 |
| 13 | " | (N,N'-bis(2-mercaptophenyl)ethylenediamine structure) | 1020 |
| 14 | " | Compound of formula 6 | 1060 |
| 15 | " | Compound of formula 8 | 1015 |
| 16 | (vanadyl hexadecachlorophthalocyanine structure) | (N,N'-bis(2-mercaptophenyl)ethylenediamine structure) | 995 |
| 17 | " | Compound of formula 6 | 1010 |
| 18 | " | Compound of formula 14 | 980 |
| 19 | C.I. Pigment Green 7 (Phthalocyanine Green) | (N,N'-bis(2-mercaptophenyl)ethylenediamine structure) | 906 |
| 20 | Compound of formula 17 | Compound of formula 6 | 859 |

Comparative Example 1

In 200 ml of DMI, 10.0 g (8.87 mmol) of C.I. Pigment Green 7 ("Phthalocyanine Green"), 21.1 g (88.70 mmol, 10 times equivalent) of a 2-(n-octylamino)thiophenol and 39.2 g (283.63 mmol, 32 times equivalent) of potassium carbonate were reacted at 170° C. for 2 hours. After the reaction mixture was allowed to cool down to room temperature, it was poured into 500 ml of methanol. The resulting precipitate was collected by suction filtration, washed successively with methanol and water and then dried, whereby 15.3 g of a near infrared absorber containing a compound represented by the following formula (16):

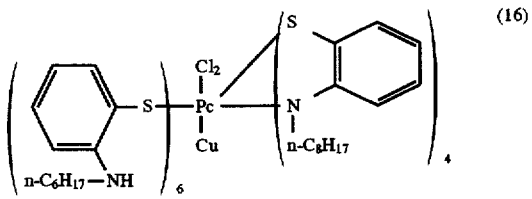

were obtained.

Figure 6:
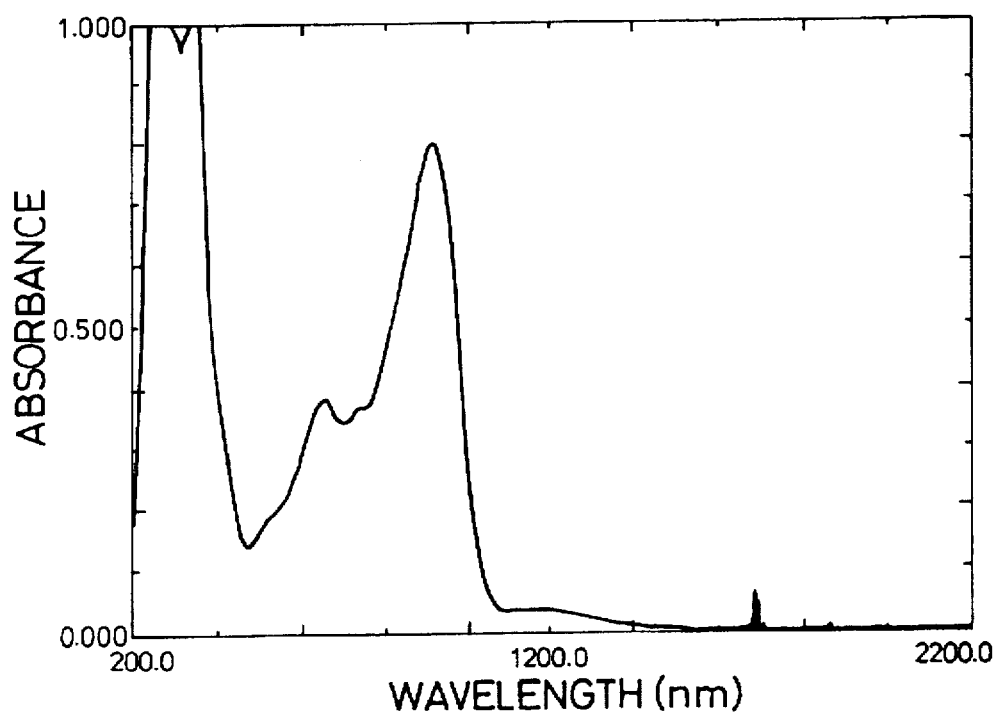
FIGS. 6, 7 and 9 are absorption spectra of near infrared absorbing mixture obtained in Comparative Examples 1, 2 and 4, respectively.

An absorption spectrum of the resulting mixture in chloroform is shown in FIG. 6. As is apparent from the figure, the absorber so obtained has an absorption peak narrower than those obtained in the above Examples and shows less absorbance of the near infrared rays not shorter than 1,000 nm.

Comparative Example 2

In a similar manner to Comparative Example 1 except that 34.4 g (159.66 mmol, 18 times equivalent) of 2-(benzylamino)thiophenol, a reaction and post-treatments were conducted, whereby 15.6 g of a near infrared absorber were obtained.

Figure 7:
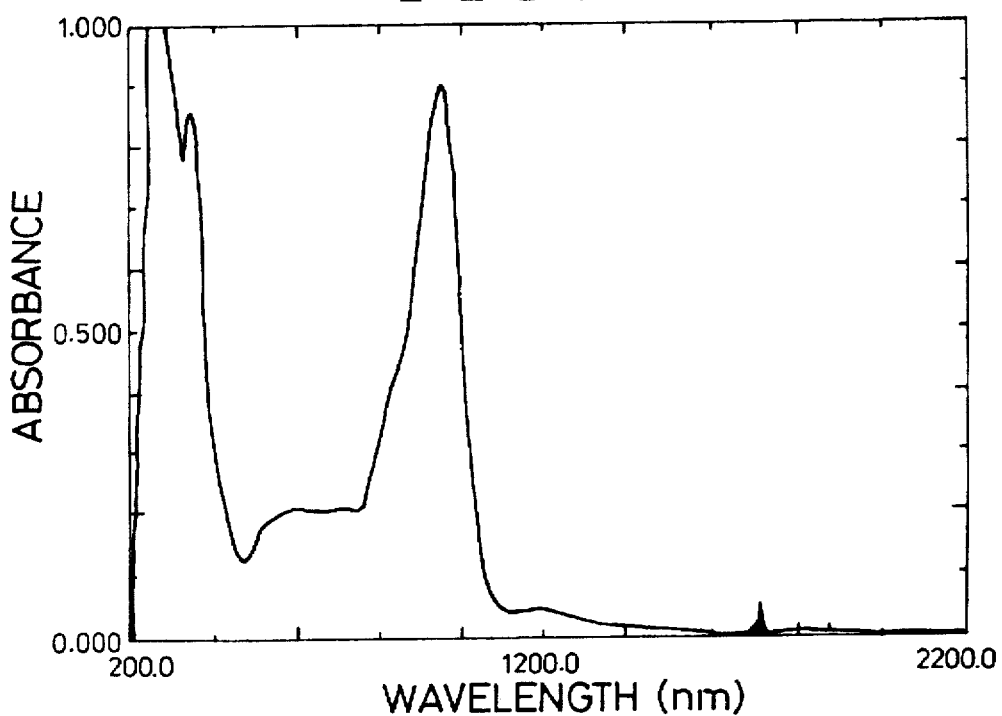

An absorption spectrum of the absorber so obtained in chloroform is shown in FIG. 7. As is apparent from the figure, the absorber has an absorption peak narrower than those obtained in the above Examples and shows less absorbance of the near infrared rays not shorter than 1,000 nm.

Comparative Example 3

Figure 8:
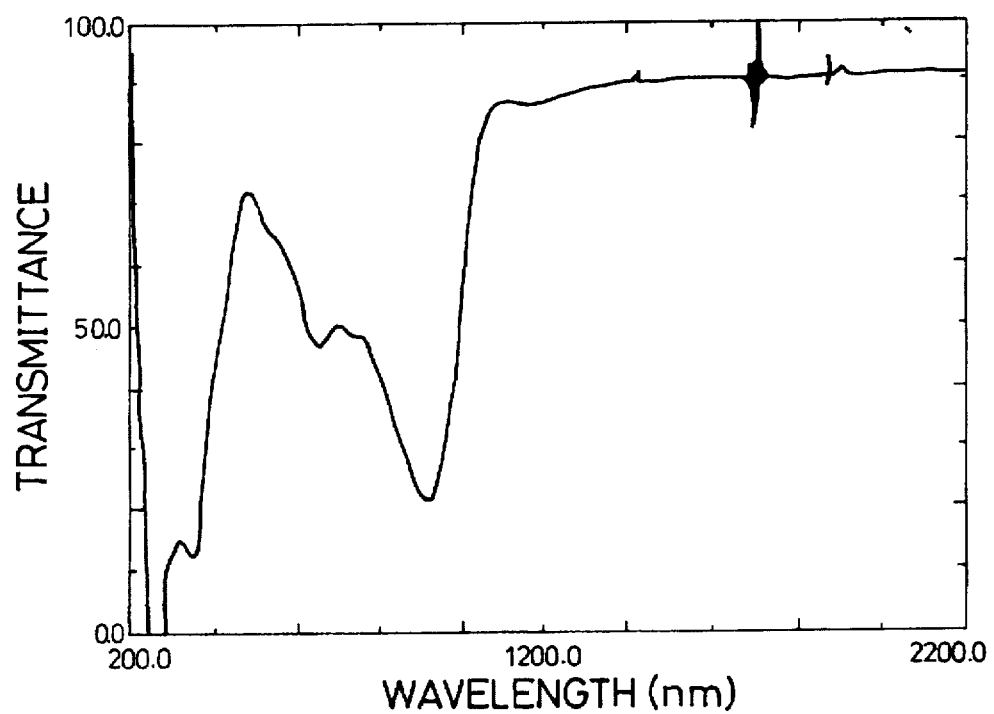
FIGS. 8 and 10 are transmittance spectra of heat-ray absorbing films obtained in Comparative Examples 3 and 5, respectively.

In a similar manner to Example 6 except that the near infrared absorber prepared in Comparative Example 1 was used instead of the near infrared absorber prepared in Example 1, a heat-ray absorbing film was produced. A transmittance spectrum of the film so obtained is shown in FIG. 8. As is apparent from the figure, the film has an transmittance greater than the film obtained in Example 6 and shows less absorbance of the near infrared rays not shorter than 1,000 nm.

Comparative Example 4

In accordance with the process disclosed in Japanese Patent Laid-Open No. 062878/1991, a copper phthalocyanine represented by the following formula (17):

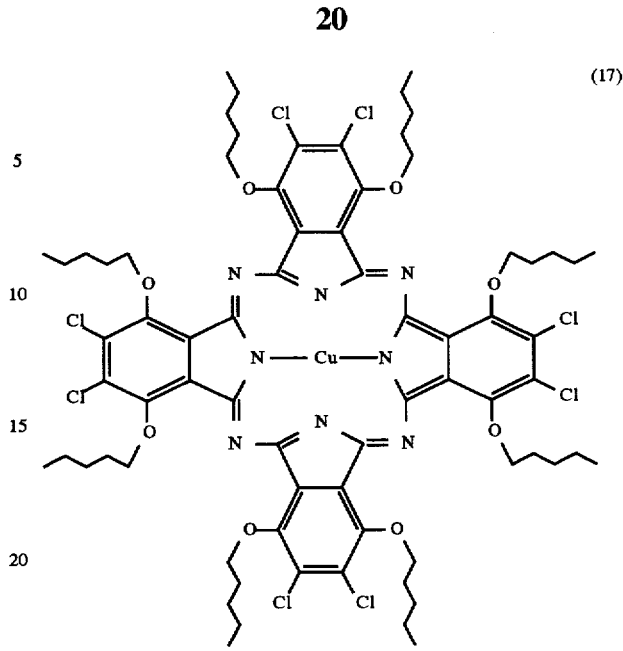

was synthesized.

Figure 9:
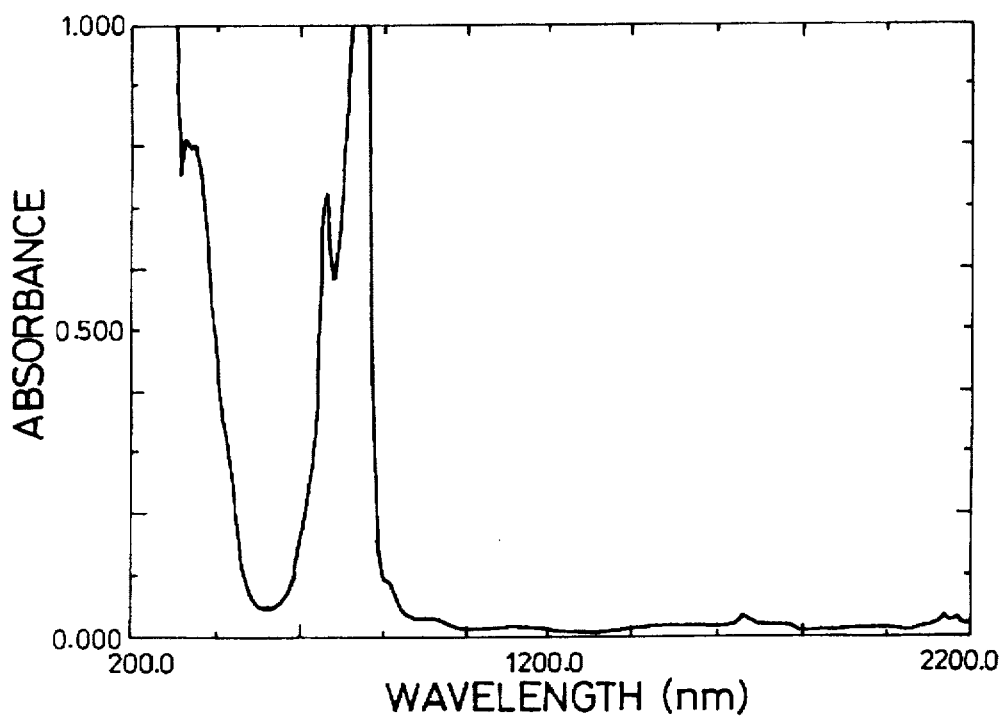

An absorption spectrum of the compound in chloroform is shown in FIG. 9. As is apparent from the figure, the compound has an absorption peak narrower than those obtained in the above Examples and shows less absorption of the near infrared rays not shorter than 1,000 nm.

Comparative Example 5

Figure 10:
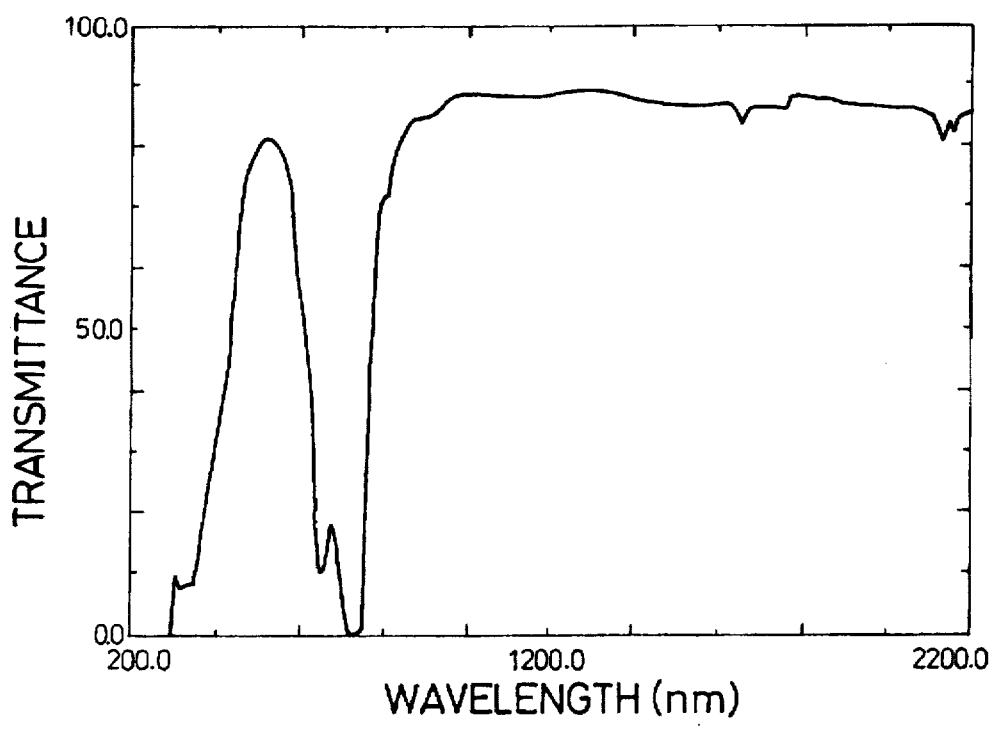

In a similar manner to Example 7 except that the phthalocyanine prepared in Comparative Example 4 was used instead of the near infrared absorber prepared in Example 2, a heat-ray absorbing film was produced. A transmittance spectrum of the film so obtained is shown in FIG. 10. As is apparent from the figure, the film has an transmittance greater than the film obtained in Example 7 and shows less absorbance of the near infrared rays not shorter than 1,000 nm.

Comparative Example 6

In accordance with the process disclosed in Japanese Patent Publication No. 75916/1992, penta(phenyl-1-amino-2-thio-ylen)-penta(2-aminophenylthio)-phthalocyanine copper was prepared. In accordance with the procedures of Examples 6 and 7, production of a pigment-kneaded PET film and a pigment-coated PET film were attempted. The hazing phenomenon due to low solubility of the compound in the resins, however, prevented the production of transparent films.

What is claimed is:

1. A phthalocyanine near infrared absorber having a broad absorption range in the near infrared region and represented by the following formula (1):

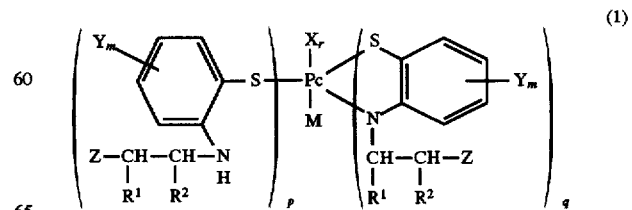

wherein $R^1$ and $R^2$ each independently represents a hydrogen atom, a $C_{1-20}$ alkyl group a $C_{6-20}$ aryl group; Ys each independently represents a $C_{1-20}$ alkyl group, a $C_{6-20}$ aryl group, a $C_{1-20}$ alkoxy group, or a $C_{6-20}$ aryloxy group; m stands for an integer of 0 to 4; Pc represents a phthalocyanine nucleus; Z represents an —SH group or an —NHR$^3$ group in which R$^3$ represents a hydrogen atom, a $C_{1-20}$ alkyl group or a $C_{6-20}$ aryl group; Xs each independently represents a halogen atom, a hydroxy group, a $C_{1-20}$ alkoxy group, a $C_{6-20}$ aryloxy group, a $C_{1-20}$ alkylthio group, a $C_{6-20}$ arylthio group, a $C_{1-20}$ alkylamino group, a $C_{6-20}$ arylamino group and a $C_{7-20}$ alkylarylamino group; the adjacent pairs of Xs may form a 5- or 6-membered ring via two hetero atoms; M represents a divalent metal atom, a monosubstituted trivalent, a disubstituted tetravalent metal or an oxymetal atom; p stands for an integer of 1 to 16; q stands for an integer of 0 to 8; r stand for an integer of 0 to 8; and p+2q+r is not greater than 16.

2. A process for the preparation of the phthalocyanine near infrared absorber according to claim 1, which comprises reacting in the presence of a base a phthalocyanine represented by the following formula (2):

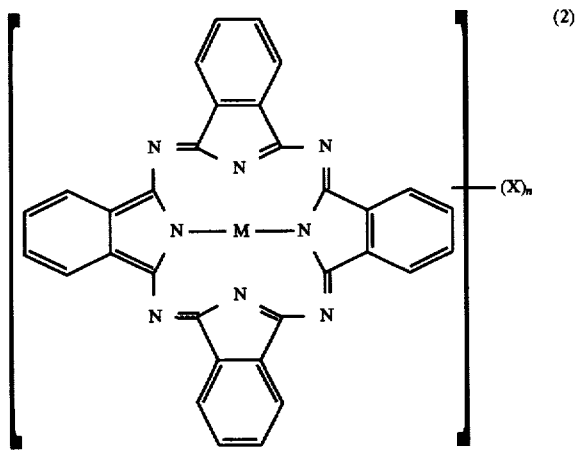

(2)

wherein Xs each independently represents a halogen atom, a hydroxy group, a $C_{1-20}$ alkoxy group, $C_{6-20}$ aryloxy group, a $C_{1-20}$ alkylthio group, a $C_{6-20}$ arylthio group, a $C_{1-20}$ alklamino group, a $C_{6-20}$ arylamino group and a $C_{7-20}$ alkylarylamino group; the adjacent pairs of Xs may form a 5- or 6-membered ring via two hereto atoms; M represents a divalent metal atom, a monosubstituted trivalent, a disubstituted tetravalent metal or an oxymetal atom, n stands for an integer of 4 to 16, with the proviso that at least four of the Xs each represents a halogen tom, with at least one 2-aminothiophenol derivative represented by the following formula (3):

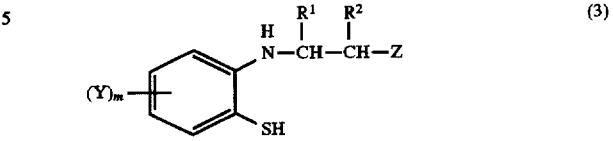

(3)

wherein R$^1$ and R$^2$ each independently represents a hydrogen atom, a $C_{1-20}$ alkyl group or a $C_{6-20}$ aryl group; Ys each independently represents a $C_{1-20}$ alkyl group, a $C_{6-20}$ aryl group, a $C_{1-20}$ alkoxy group, or a $C_{6-20}$ aryloxy group; Z represents an —SH group or an —NHR$^3$ group in which R$^3$ represents a hydrogen atom, a $C_{1-20}$ alkyl group or a $C_{6-20}$ aryl group; and m stands for an integer of 0 to 4.

3. The process according to claim 2, wherein the 2-aminothiophenol derivative is a compound represented by the following formula (4):

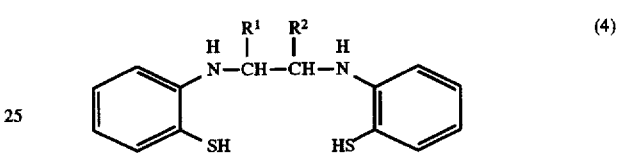

(4)

wherein R$^1$ and R$^2$ each independently represents a hydrogen atom, a $C_{1-20}$ alkyl group or a $C_{6-20}$ aryl group.

4. The process according to claim 2, wherein M represents Cu, AlCl, TiO or VO.

5. The process according to claim 2, wherein each X represents a halogen atom.

6. The process according to claim 5, wherein the phthalocyanine represented by formula (2) is C.I. Pigment Green 7, C.I. Pigment Green 36, C.I. Pigment Green 37 or C.I. Pigment Green 38.

7. A phthalocyanine near infrared absorber having a broad-absorption range in the near infrared region, which has been obtained by the process according to claim 2.

8. A near infrared absorbing resin composition comprising the near infrared absorber according to claim 1.

9. A heat-ray absorbing filter comprising the near infrared absorber according to claim 1.

* * * * *